United States Patent [19]
Dillon

[11] Patent Number: 5,172,688
[45] Date of Patent: Dec. 22, 1992

[54] NASAL-GASTRIC TUBE HOLDER

[75] Inventor: Michael M. Dillon, Scottsdale, Ariz.

[73] Assignee: Innovative Medical Design Corp., Hicksville, N.Y.

[21] Appl. No.: 743,173

[22] Filed: Aug. 9, 1991

[51] Int. Cl.⁵ .............................. A61M 25/02
[52] U.S. Cl. .................. 128/207.18; 128/DIG. 26; 604/180
[58] Field of Search ............ 128/207.14, 207.18, 128/DIG. 26; 604/180

[56] References Cited

U.S. PATENT DOCUMENTS

| | | | |
|---|---|---|---|
| 3,046,989 | 7/1962 | Hill | 128/207.18 |
| 4,120,304 | 10/1978 | Moor | 128/DIG. 26 |
| 4,307,903 | 12/1981 | Wallace | 128/207.14 |
| 4,645,492 | 2/1987 | Weeks | 604/180 |
| 4,658,813 | 4/1987 | Jones | 128/207.14 |
| 4,823,789 | 4/1989 | Reisang, III | 128/207.18 |
| 4,846,170 | 7/1989 | McAnalley et al. | 128/207.13 |
| 4,915,694 | 4/1990 | Yamamoto et al. | 604/180 |

Primary Examiner—Clifford D. Crowder
Assistant Examiner—Stephen R. Funk
Attorney, Agent, or Firm—Bauer & Schaffer

[57] ABSTRACT

A planar flexible body, which generally assumes the shape of the nose when disposed thereon is provided. The body is provided with a hub having a lengthwise slit so that the hub can be easily spread apart in a lengthwise direction to permit insertion, retention, and removal of the gastrointestinal tube in the hub.

9 Claims, 3 Drawing Sheets

NASAL-GASTRIC TUBE HOLDER

FIELD OF THE INVENTION

This invention relates to a medical device and, in particular, to a nasal-gastric tube holder.

BACKGROUND OF THE INVENTION

A wide variety of gastrointestinal tube holders and/or anchoring devices are known such as, for example, those disclosed U.S. Pat. Nos. 4,120,304; 4,633,863; 4,738,662; 4,804,374; 4,838,878; 4,932,943; and 4,986,815. While these and other known devices are useful for their intended purposes, they generally are of rather complex structure or comprise a plurality of parts, thus necessitating more handling and manipulation when in use as well as often necessitating detailed close surveillance when in use.

Specifically, the prior art devices comprise a pad, capable of being attached to the patient's face or nose, to which is attached securement means such as clips, clamps, metal connectors, extra sleeves, or the like. It is these added means which make such holders difficult to attach to the patient and/or make it difficult to attach or retain the tube firmly or securely to the holder. A particular problem lies in the fact that such securement means are remote from the nasal passage, subject to inadvertent opening or dislodgement on movement of the patient and thereby allow the tube to move out of position.

There exists, therefore, a need for a nasal-gastric tube holder or anchor which does not exhibit the above-mentioned disadvantages. The present invention satisfies such a need.

BRIEF STATMENT OF THE INVENTION

In accordance with the invention there is provided a nasal-gastric tube holder comprising a thin, planar, flexible body member having upper and lower surfaces, the lower surface having applied to it an adhesive capable of securing the body to the nose of the patient and allowing the body member to generally assume the shape of the nose when it is disposed thereon. An integrally formed hub, provided with a central bore, is located on the body member near the entrance to a nasal passage. The hub is split lengthwise, allowing the hub to be easily spread apart to permit the insertion, firm retention, and removal of the nasal-gastric tube in the bore.

Preferably, the body is made of soft, pliable plastic resin or rubber-like material so as to be capable of assuming the shape of the nose and to be soft and neither annoying nor harmful to the patient. The body ma be provided with a fan or wing-like shape to facilitate matching to the contour of the nose and face. The body is preferably provided with perforations to permit air to pass, thus allowing the skin to breathe, thereby avoiding necrosis of the skin. Further, a central rib may be provided, conforming to the position of the bridge of the nose, which rib may be somewhat more rigid than the rest of the body so as to constitute a guide for application and a means for stabilization of the anchor in use.

Full details of the present invention are set forth in the following description and in the accompanying drawings.

BRIEF DESCRIPTION OF THE DRAWINGS

In order to understand the invention more fully, reference is directed to the accompanying drawings, which are to be taken in conjunction with the detailed description of the invention and in which drawings.

DETAILED DESCRIPTION OF THE INVENTION

Figure 1:
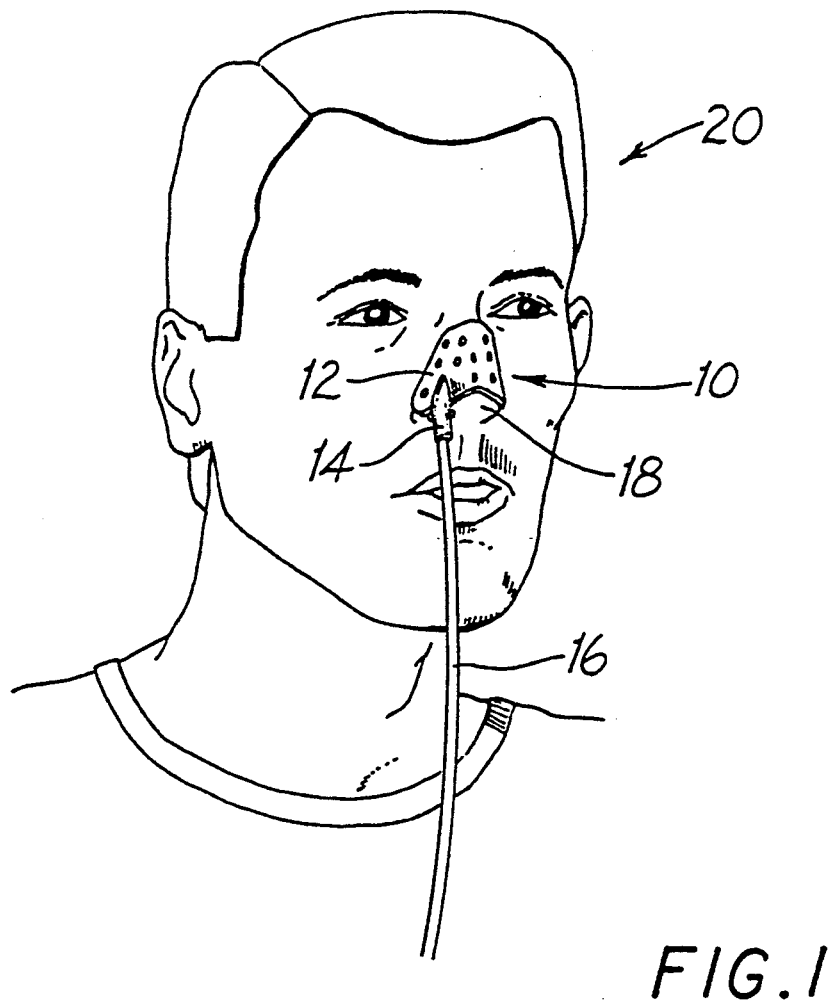
FIG. 1 is a perspective view of the patient, to which the nasal-gastric tube holder embodying the present invention is attached.
Figure 2:
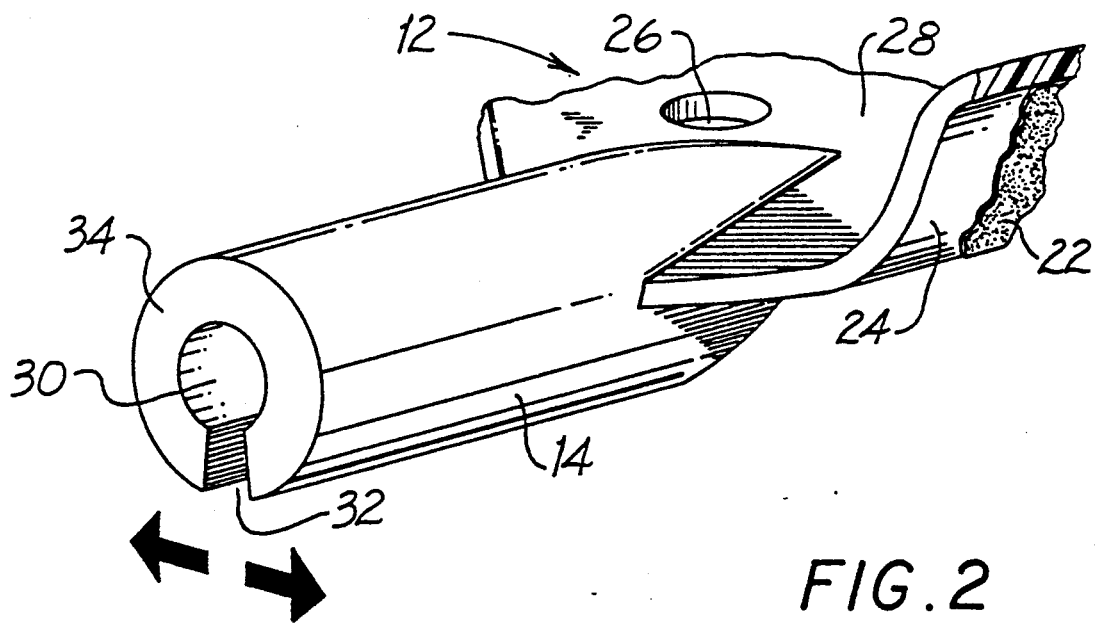
FIG. 2 is an enlarged view of the holder shown in FIG. 1, partially fragmented.
Figure 3:
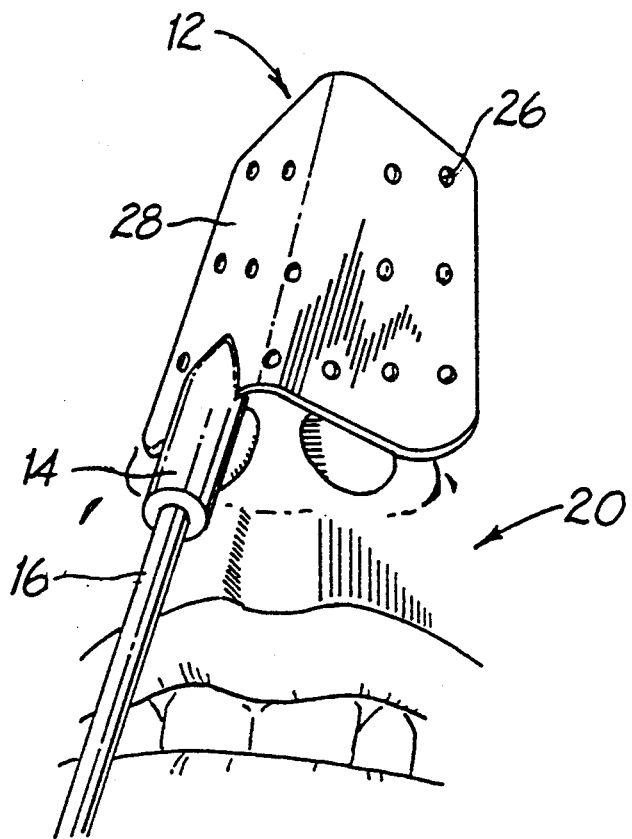
FIG. 3 is an enlarged view of the patient's nose, showing the holder of FIG. 1 in place.
Figure 4:
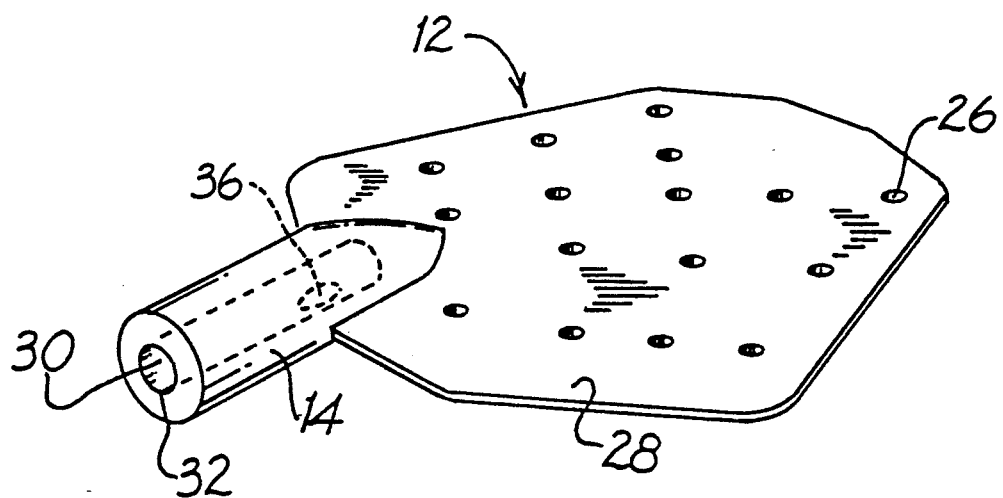
FIG. 4 is a perspective view of the holder of the present invention.

Referring now to FIG. 1, the nasal-gastric tube holder of the present invention, generally referred to by the numeral 10, comprises a generally thin, planar flexible body member 12 having a hub 14 holding a nasal-gastric tube 16 and a flat flexible configuration shaped for plastic adhesion on the nose 18 of a patient generally referred to by the numeral 20. The body 12 is adhered to the skin of the patient by applying a hypo-allergenic adhesive coating 22 to the lower surface 24 of the body member 12. The body member 12 may be made of silicone material, medical grade rubber, or other plastic resin material. Medical grade silicone and rubber materials are known and are readily available through commercial medical supply channels.

The body member is provided with a plurality of holes or openings 26 which extend from the upper surface 28 to the lower surfaces 24, thus permitting the pores of the skin of the patient to breathe even during lengthy application and use, thus avoiding necrosis.

The hub 14 and the body 12 are preferably formed integrally with each other by molding or other conventional means. The hub is provided with a central bore 30, which may, if desired, taper from its outer end toward its inner end to more readily hold the tube 16. The hub has an enlarged wall 34 so as to be less flexible than the body. This lowered flexibility acts to maintain the tube 16, where prominal to the nose, stable so as not to unduly flex and irritate the nasal passage. The hub is provided with a slit 32 running lengthwise, allowing the hub to be distended and spread apart for reception, retention, and removal of the tube 16. Because the hub wall 34 is relatively thick, it has a resilient memory and is easily closeable about the tube 16, thus securly holding the tube.

The bore may be tapered from proximal end to distal end so as to add to the frictional engagement between hub and tube. The slit may be enlarged so that on closing of the hub the bore takes on an a-circular or elliptical shape, dependent on the space between the edges of the slit, thus also providing an increased grasp on the tube. The spreading of the tube allows a variety in the sizes of tubes used with the same holder.

Figure 5:
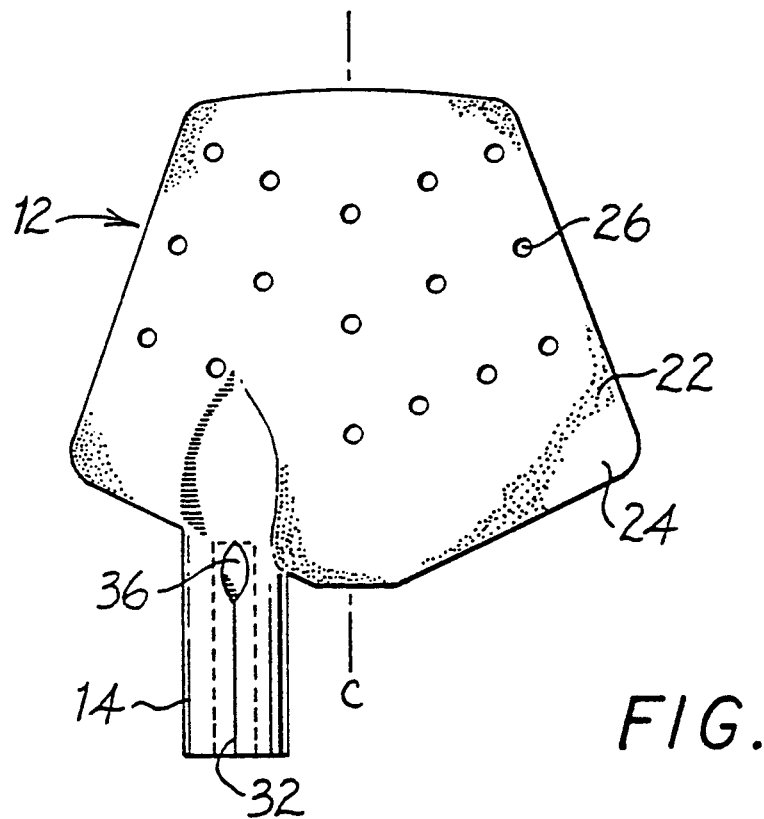
FIG. 5 is a bottom plan view of the holder shown in FIG. 4.

The bore 30 terminates at the distal end in an elliptical opening 36 (FIG. 5), allowing the inserted tube 16 to pass freely from the bore 30 into the nasal passage of the patient. The hub 14 is formed on either side of the median axis of the body 12 so as to be in line with either the right or left nostril. In production, some holders 10 will be made with left nostril hubs, and some will be made with right nostril hubs so that the physician or surgeon will be able to select which is to be used. For greater comfort to the patient, the physicians may alternate between the two nostrils.

In use the holder of this invention allows the physician to insert the nasal-gastric tube through the patient's nose without first attaching the tube to the holder, although the tube may be secured to the patient initially. Once the tube 16 has been inserted through a patient's nasal passage, it is simply attached to the holder 10 by spreading the hub 14 along its slit 32, inserting the tube and allowing the hub to clamp over the tube, after which the body member 12 is attached to the patient's nose if it is not already there.

Figure 6:
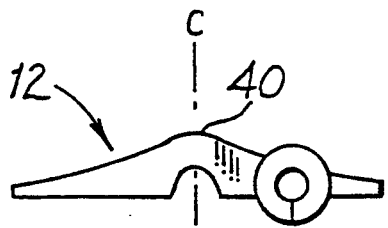
FIG. 6 is a sectional view of the holder, illustrating the cross sectional structure thereof and the position of the hub.
Figure 7:
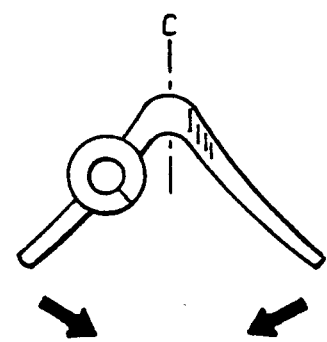
FIG. 7 is a view similar to that of FIG. 6, showing another cross sectional structure.

As seen in FIGS. 6 and 7, the cross section of the planar body may be varied in thickness so as to be slightly thicker along its centerline C. The thickness may be so increased that a rib 40 may be created along the center line. Such rib not only provides stability to the body but also provides the physician with a guide placeable over the bridge of the nose. FIGS. 6 and 7 also show the placement of the hub on either the right or left side. Still further, the planar body may be shaped along the center line so as to facilitate flexing and shaping of the body to the nose.

A holder in accordance with the invention may have a body member approximately 1/16" thick and a hub having an approximately ⅜" outside diameter and an internal diameter of ⅛". The internal diameter may taper down from 3/16" at the outer end to 1/8" at the inner portion of the hub. Overall, the holder of this invention, when arranged on a flat surface before use, has sides which rest at 70 degree angles to its center line, front to rear. The holder, not including the hub, has an overall length of about 2", from front to rear, along the center line.

Hypo-allergenic skin adhesives are commonly used in the field of medical devices. Any such adhesives may be used. The adhesive may be applied by the physician in situ, or it may be applied during the process of manufacturing the anchor so that the physician may be freed of the task of the application of the adhesive. Removal of the anchor from the skin is easily accomplished, and the skin may be easily cleaned using isopropyl alcohol or the like.

The tube holder of the present invention has numerous advantages. For example, it is simple in structure, being a one piece disposable apparatus which can be formed by known plastic molding processes and fabricating processes with readily available materials.

Moreover, the hub holds the nasal-gastric tube frictionally in place since it is similarly made of silicone or rubber-like material. Slippage between the two is prevented. The holder can be easily lifted up from the nose of a patient, although once it is in place, it will retain the tube in a substantially fixed position. This alleviates rubbing of the nasal-gastric tube on the inside of the nose and avoids irritation of the edges of the nose as well. It will also be difficult for the patient to pull the tube out of his nose or for the tube to come out of the nose accidentally because of the adherence of the tube to the bore of the hub.

While the above description contains many specificities, these should not be construed as limitations on the scope of the invention but rather as an exemplification of the preferred embodiment thereof. Accordingly, the scope of the instant invention should not be determined by the embodiment described but by the claims appended hereto and their legal equivalents.

What is claimed is:

1. A holder for attaching a nasal-gastric tube to the nose of a patient having a pair of nasal passages, said holder comprising an elastomeric planar flexible body having an upper and lower surface and a central axis, said body generally assuming the shape of the nose when disposed thereon and having a rigid elastomeric cylindrical hub provided with a central bore located offset from the central axis, said hub being integrally formed with the body, said hub having a proximal end and a distal end, said bore terminating at said distal end in an opening in the lower surface of said body in proximity to one of the nasal passages and a lengthwise split for spreading said hub apart to permit insertion in and removal of said nasal-gastric tube from said bore and for closing upon the tube inserted therein for frictional retention of said tube.

2. The holder according to claim 1, including adhesive means on the lower surface of said body.

3. The holder according to claim 1, wherein the body is provided with a plurality of openings through the surface thereof.

4. The holder according to claim 1, wherein the body and hub are made of flexible resilient silicone material.

5. The holder according to claim 4, wherein the hub is made of silicone which is less flexible than the flexible silicone from which the body is made.

6. The holder according to claim 1, wherein said slit is enlarged so that upon closing of the edges of the slit on each other, the bore is acircular in cross section.

7. The holder according to claim 1, wherein the hub is located on the body to the left of the central axis of said body member.

8. The holder according to claim 1, wherein the hub is located on the body to the right of the central axis of said body.

9. The holder according to claim 1, wherein said bore is tapered from the proximal end to the distal end of said hub.

* * * * *